United States Patent
Takeuchi

(10) Patent No.: US 9,689,831 B2
(45) Date of Patent: Jun. 27, 2017

(54) SENSOR DISCHARGE MECHANISM FOR A BIOLOGICAL INFORMATION MEASUREMENT DEVICE

(71) Applicant: PANASONIC HEALTHCARE HOLDINGS CO., LTD., Minato-Ku, Tokyo (JP)

(72) Inventor: Yoshiki Takeuchi, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 588 days.

(21) Appl. No.: 14/370,488

(22) PCT Filed: Jan. 11, 2013

(86) PCT No.: PCT/JP2013/000076
§ 371 (c)(1),
(2) Date: Jul. 3, 2014

(87) PCT Pub. No.: WO2013/105508
PCT Pub. Date: Jul. 18, 2013

(65) Prior Publication Data
US 2015/0014159 A1    Jan. 15, 2015

(30) Foreign Application Priority Data
Jan. 13, 2012 (JP) .................................. 2012-005000

(51) Int. Cl.
*G01N 27/26* (2006.01)
*G01N 27/327* (2006.01)
(Continued)

(52) U.S. Cl.
CPC ....... *G01N 27/327* (2013.01); *A61B 5/14532* (2013.01); *B01L 9/52* (2013.01); *G01N 27/3273* (2013.01); *G01N 33/4875* (2013.01)

(58) Field of Classification Search
CPC .................. G01N 27/327; G01N 27/3273
(Continued)

(56) References Cited

U.S. PATENT DOCUMENTS 8,233,956 B2   7/2012  Ohama et al.
8,696,597 B2   4/2014  Neel et al.
(Continued)

FOREIGN PATENT DOCUMENTS

JP   2003-114213 A   4/2003
JP   2005-111135 A   4/2005
(Continued)

OTHER PUBLICATIONS

Decision to Patent from the corresponding Japanese Patent Application No. 2013-553269 issued on Mar. 10, 2015.
(Continued)

*Primary Examiner* — Jill Warden
*Assistant Examiner* — Brittany Fisher
(74) *Attorney, Agent, or Firm* — Shinjyu Global IP

(57) ABSTRACT

An engagement component that engages with the rear part of a sensor mounted to a sensor connector, and a manipulation body that moves this engagement component to a sensor insertion opening side are provided. In addition, there are provided a manipulation rod that is engaged at one end with the manipulation body and whose other end is pulled out of a main body case through a through-hole provided to the main body case, and a manipulation component that is linked to the other end side of this manipulation rod. The device further comprises an annular wall that is provided outside the main body case and around a through-hole, and a metal slide bearing that covers this annular wall, and a resin sliding member that is slid with respect to a metal slide bearing is provided on the metal slide bearing side of the manipulation component.

12 Claims, 5 Drawing Sheets

(51) Int. Cl.
  *B01L 9/00* (2006.01)
  *A61B 5/145* (2006.01)
  *G01N 33/487* (2006.01)

(58) Field of Classification Search
  USPC ........................................................ 204/400
  See application file for complete search history.

(56) References Cited

U.S. PATENT DOCUMENTS

| | | |
|---|---|---|
| 2005/0149090 A1 | 7/2005 | Morita et al. |
| 2005/0224345 A1* | 10/2005 | Taniike .............. G01N 33/4875 204/403.01 |
| 2006/0133956 A1* | 6/2006 | Hamanaka ................ B01L 9/52 422/68.1 |
| 2007/0233395 A1 | 10/2007 | Neel et al. |
| 2009/0108013 A1* | 4/2009 | Van Der Velde .. G01N 33/4875 221/1 |
| 2009/0204139 A1 | 8/2009 | Morita et al. |
| 2009/0227854 A1 | 9/2009 | Ohama et al. |
| 2010/0012530 A1* | 1/2010 | Watanabe .......... A61B 5/14532 205/792 |
| 2012/0116706 A1 | 5/2012 | Nakanishi et al. |

FOREIGN PATENT DOCUMENTS

| | | |
|---|---|---|
| JP | 2009-210278 A | 9/2009 |
| JP | 2009-532706 A | 9/2009 |
| JP | 2009-236790 A | 10/2009 |
| WO | 2011/001917 A1 | 1/2011 |

OTHER PUBLICATIONS

International Search Report from No. PCT/JP2013/000076 Issued on Feb. 19, 2013.

* cited by examiner

SENSOR DISCHARGE MECHANISM FOR A BIOLOGICAL INFORMATION MEASUREMENT DEVICE

PRIORITY

This application claims priority to International Application PCT/JP2013/000076, with an international filing date of Jan. 11, 2013 which claims priority to Japanese Patent Application No. JP2012-005000 filed on Jan. 13, 2012. The entire disclosures of International Application PCT/JP2013/000076 and Japanese Patent Application No. JP2012-005000 are hereby incorporated herein by reference.

TECHNICAL FIELD

The present invention relates to a biological information measurement device that measures blood glucose levels from blood, or other such biological information.

BACKGROUND

A biological information measurement device is provided with a main body case having a sensor insertion opening, and a sensor discharge mechanism for discharging a sensor mounted to this sensor insertion opening to outside the sensor insertion opening.

After biological information has been measured, the sensor is discharged from the sensor insertion opening by the sensor discharge mechanism, and that sensor is discarded (see Patent Literature 1: JP2009-532706A, for example).

With this prior art, after biological information has been measured, the sensor is discharged from the sensor insertion opening by the sensor discharge mechanism, and that sensor is discarded, so the work involved is easy. That is, when the sensor is discarded, the user does not need to pull out the sensor with his fingers through the sensor insertion opening, and can discharge the sensor from the sensor insertion opening and discard the sensor just by operating the sensor discharge mechanism.

This sensor discharge mechanism comprises an engagement component that engages with the rear part of the sensor mounted to a sensor connector provided inside the main body case, and a manipulation body that moves this engagement component to the sensor insertion opening side. It further comprises a manipulation rod that is engaged at one end with the manipulation body and whose other end is pulled out of the main body case through a through-hole provided to the main body case, and a manipulation component that is linked to the other end side of this manipulation rod that is pulled out of the main body case.

With the above configuration, when the sensor is discharged, the user moves the manipulation component to the sensor insertion opening side. At this point the rear face side of the manipulation component, which is not touched by the user, slides over the surface of the main body case. Accordingly, repeated sensor discharge wears down the front face side of the main body case that is in contact with the rear face of the manipulation component or the rear face side of the manipulation component, and as a result the sensor discharge operation is not performed as smoothly, and the operation is more difficult.

SUMMARY

The biological information measurement device of the present invention comprises a main body case having a sensor insertion opening, a sensor connector provided to the rear portion of the sensor insertion opening, and a sensor discharge mechanism that discharges a sensor mounted to this sensor connector to outside the sensor insertion opening. The sensor discharge mechanism comprises an engagement component that engages with the rear part of a sensor mounted to the sensor connector, a manipulation body that moves this engagement component to the sensor insertion opening side, and a manipulation rod that is engaged at one end with the manipulation body and whose other end is pulled out of the main body case through a through-hole provided to the main body case. The sensor discharge mechanism further comprises a manipulation component that is linked to the other end side of this manipulation rod, an annular wall that is provided around the through-hole on the outside of the main body case, and a metal slide bearing that covers this annular wall. A resin sliding member is provided on the metal slide bearing side of the manipulation component, and this resin sliding member is slid with respect to the metal slide bearing.

When the manipulation component is operated during sensor discharge, the resin sliding member that is integrated with the manipulation component slides over the metal slide bearing. Since the resin sliding member, which is composed of resin, slides against the metal slide bearing, which is composed of metal, this results in extremely good sliding, which means that there is almost no wear of the resin sliding member, and as a result a state of good sliding with respect to sensor discharge can be maintained.

Another effect that can be anticipated with the present invention is that since the annular wall is provided around the through-hole in the main body case in order to provide the metal slide bearing, any water, alcohol, or other liquid used for cleaning the main body case, for example, will be less likely to infiltrate the interior of the main body case from the through-hole.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

The biological information measurement device in the first embodiment of the present invention will now be described through reference to the drawings.

First Embodiment

Figure 1:
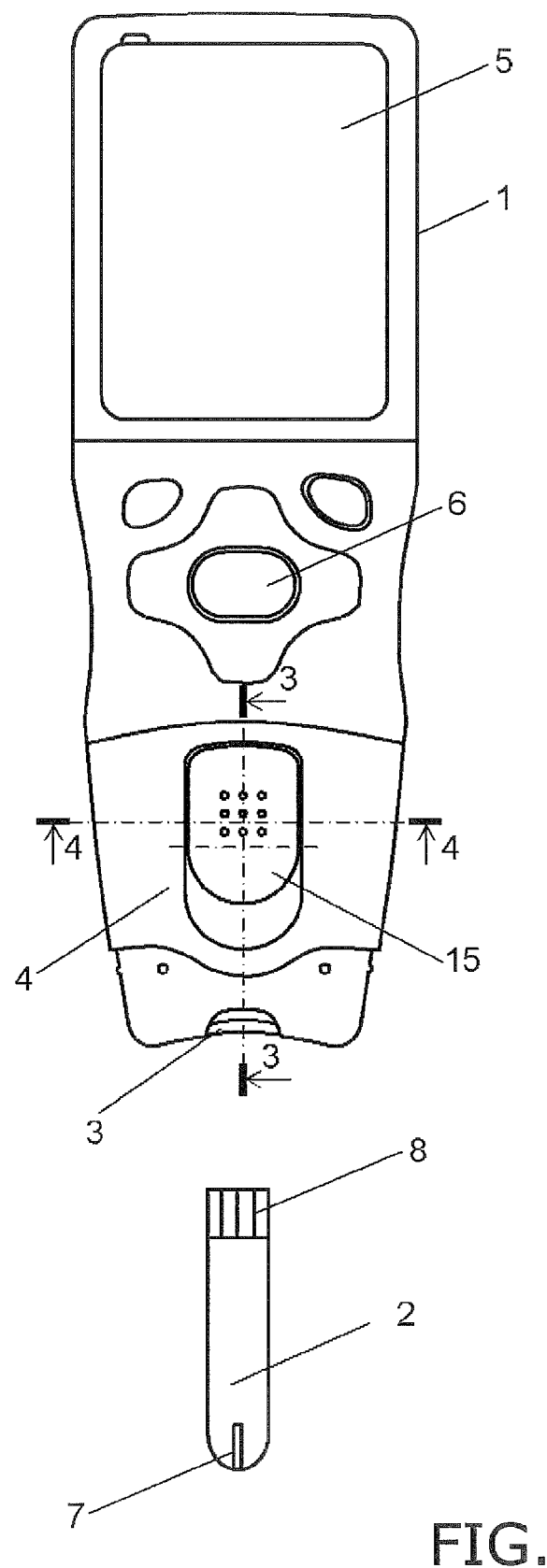
FIG. 1 is a plan view of a biological information measurement device in a first embodiment of the present invention.

As shown in FIG. 1, a sensor insertion opening 3 for inserting a sensor 2 is provided at one end of a main body case 1. A manipulation component 15, which constitutes a sensor discharge mechanism 4 for discharging the sensor 2 inserted in the sensor insertion opening 3 to the outside of the sensor insertion opening 3, is disposed at one end of the front face of this main body case 1.

A display component 5 that displays measurement results and the like is provided at the other end of the front face of the main body case 1. A typical manipulation switch 6 for turning on the power, storing or checking data, or the like, is disposed between the display component 5 and the sensor discharge mechanism 4.

In this embodiment, the sensor 2 is a sensor that measures blood glucose levels. A blood deposition component 7 is disposed at one end of the sensor 2, and an electrode component 8 is disposed at the other end of the sensor 2.

Next, the sensor discharge mechanism 4 will be described through reference to FIGS. 2 to 6.

Figure 2:
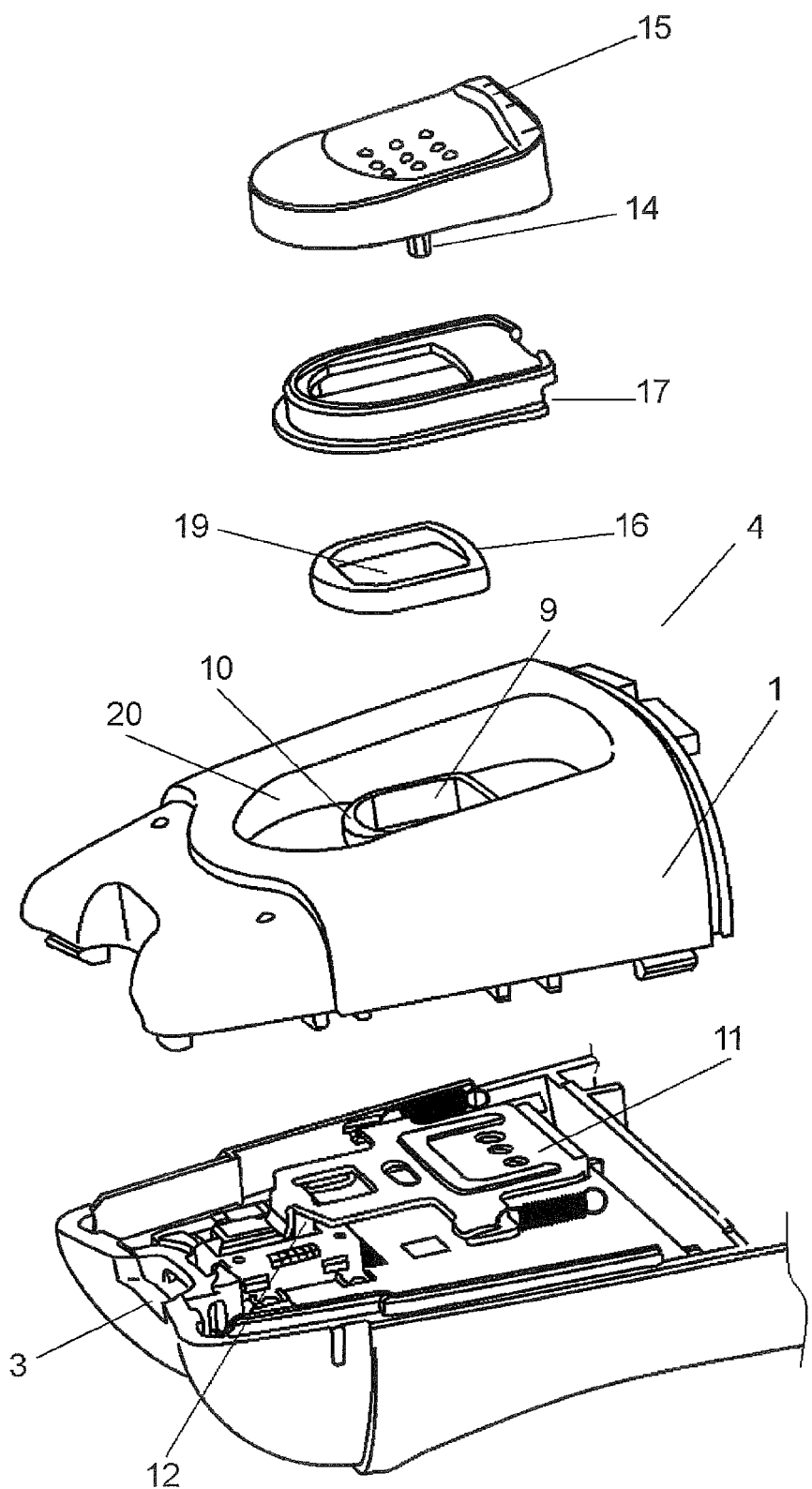
FIG. 2 is an exploded oblique view of the main components of the biological information measurement device in a first embodiment of the present invention.

First, as shown in FIG. 2, in the portion of the main body case 1 where the sensor discharge mechanism 4 is provided, a through-hole 9 is formed in the main body case 1, and an annular wall 10 that protrudes outside of the main body case 1 is provided to the front face of the main body case 1 and around this through-hole 9. A manipulation body 11 is disposed inside the main body case 1 and opposite the through-hole 9. The manipulation body 11 is disposed so that it can slide from the state in FIG. 2 to close to the sensor insertion opening 3.

Figure 3:
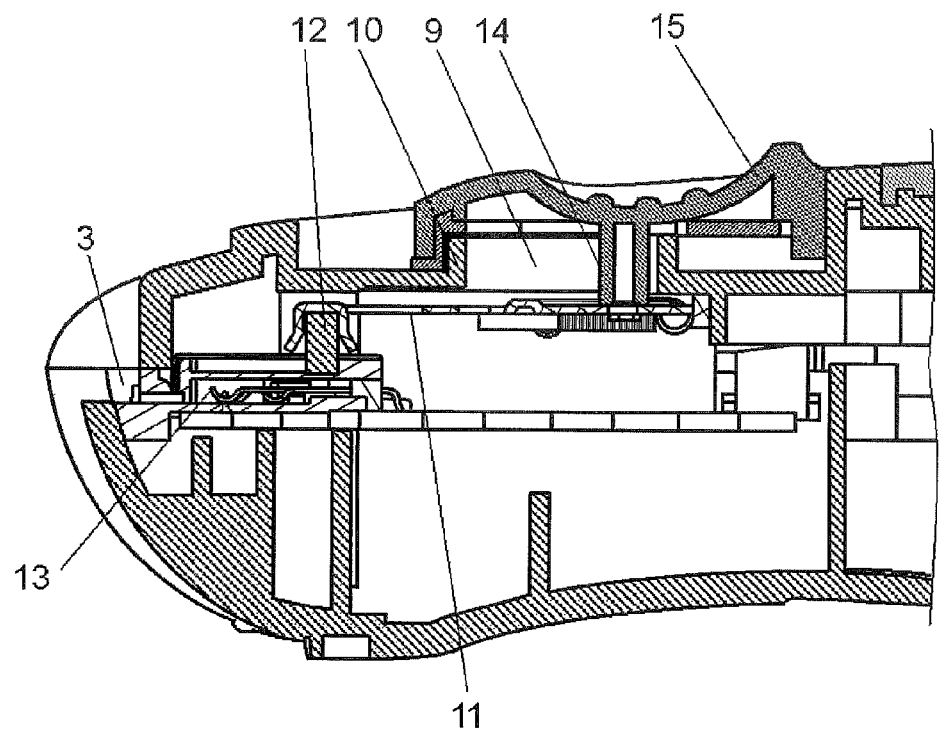
FIG. 3 is a 3-3 cross section of FIG. 1.
Figure 4:
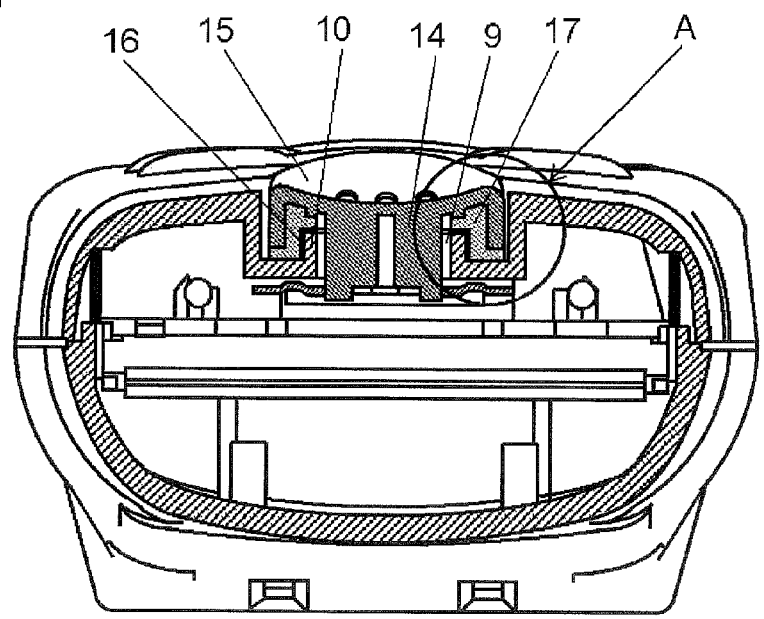
FIG. 4 is a 4-4 cross section of FIG. 1.

As shown in FIG. 3, an engagement component 12 that engages with the rear end part of the sensor 2 (see FIG. 1) inserted in the sensor insertion opening 3 is provided on the sensor insertion opening 3 side of this manipulation body 11.

In the state in FIG. 1, when the electrode component 8 of the sensor 2 is inserted through the sensor insertion opening 3 into the main body case 1, the electrode component 8 is electrically connected by touching a sensor connector 13 inside the main body case 1. When blood is deposited on the deposition component 7 in this state, the blood glucose level is measured and then displayed on the display component 5.

In this state, since the engagement component 12 shown in FIGS. 2 and 3 is engaged with the rear end part of the sensor 2 (see FIG. 1), if the sensor discharge mechanism 4 is manipulated, the electrical connection between the sensor connector 13 and the electrode component 8 of the sensor 2 is broken, and the sensor 2 is discharged from the sensor insertion opening 3 and can then be discarded.

As shown in FIGS. 2 to 5, the sensor discharge mechanism 4 for discharging the sensor 2 has the engagement component 12 that engages with the sensor 2 mounted to the sensor connector 13, and the manipulation body 11 that moves this engagement component 12 to the sensor insertion opening 3 side. In addition, the sensor discharge mechanism 4 comprises a manipulation rod 14 that is engaged at one end with the manipulation body 11 and whose other end is pulled out of the main body case 1 through the through-hole 9 provided to the main body case 1, the manipulation component 15 that is linked to the other end side of this manipulation rod 14, the annular wall 10 that is provided outside the main body case 1 and around the through-hole 9, and a metal slide bearing 16 that covers this annular wall 10.

Furthermore, the sensor discharge mechanism 4 has an annular resin sliding member 17 provided on the metal slide bearing 16 side of the manipulation component 15. This resin sliding member 17 is provided integrally on the lower face side of the manipulation component 15.

This resin sliding member 17 is slid against the metal slide bearing 16.

Figure 6A:
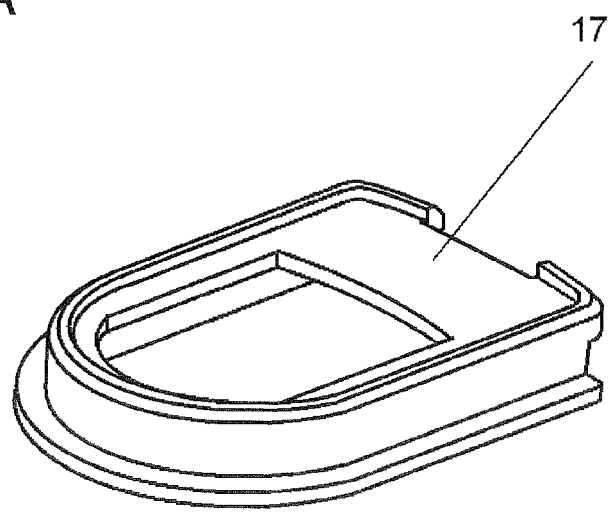
FIG. 6A is an oblique view of the resin sliding member of the biological information measurement device in a first embodiment of the present invention.
Figure 6B:
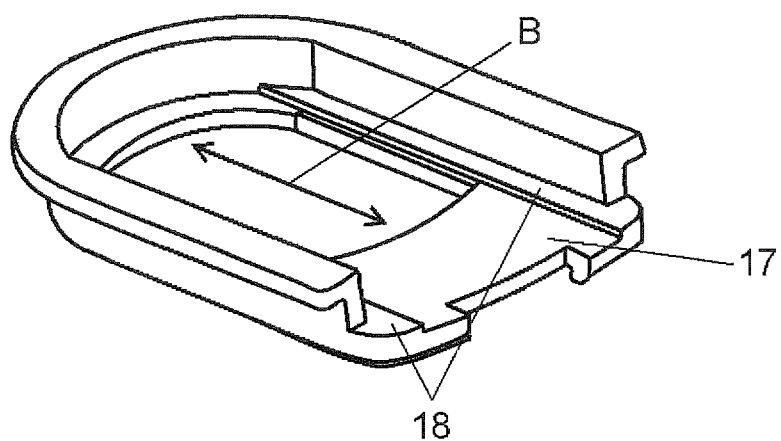
FIG. 6B is an oblique view of the resin sliding member of the biological information measurement device in a first embodiment of the present invention.

The resin sliding member 17 is formed as shown in FIGS. 6A and 6B. As shown in FIG. 6B, the configuration is such that the two side portions of the resin sliding member 17, which are arranged in a direction perpendicular to the manipulation direction of the manipulation component 15 indicated by the arrow B at the face on the metal slide bearing 16 side, protrude toward the metal slide bearing 16 side. That is, as shown in FIG. 6B, protrusions 18 that protrude to the metal slide nearing 16 side are disposed on a face on the metal slide bearing 16 side of the resin sliding member 17 (which is provided integrally on the lower face side of the manipulation component 15 (not shown)) and on both sides perpendicular to the manipulation direction of the manipulation component 15, which is the direction going from the display component 5 toward the sensor insertion opening 3 and indicated by the arrow B.

Figure 5:
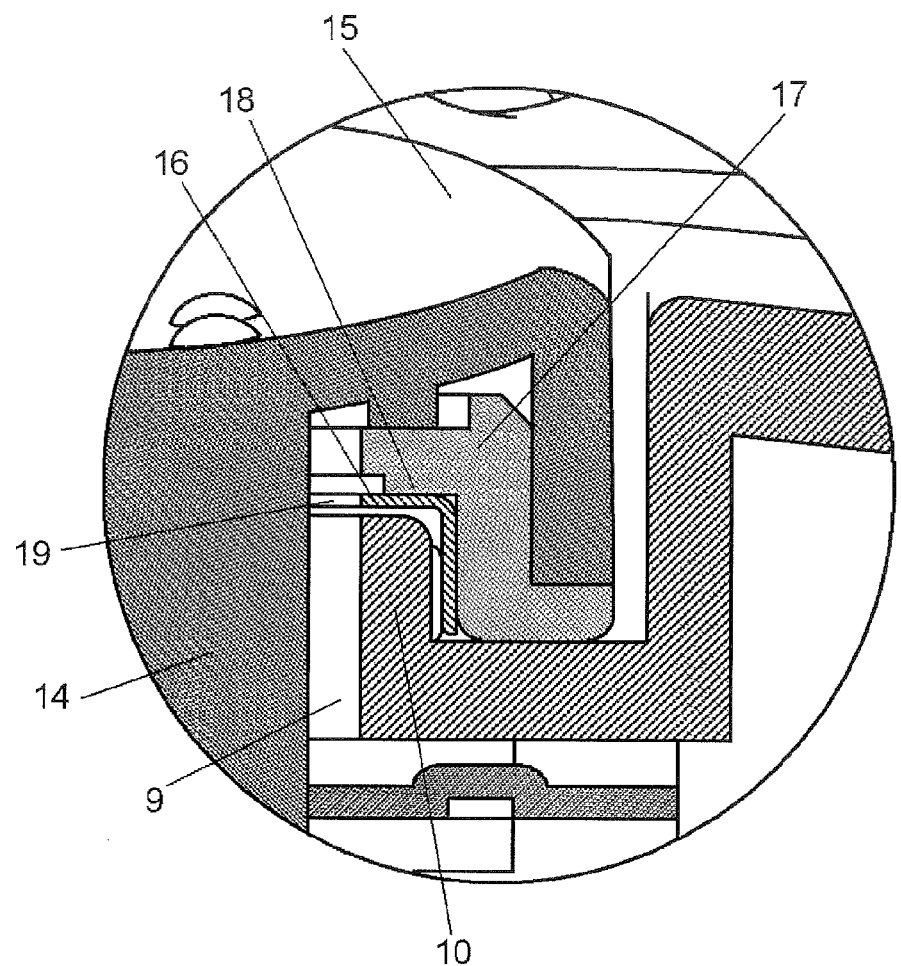
FIG. 5 is a detail cross section of portion A in FIG. 4.

As shown in FIG. 5, the protrusions 18 on the two side portions of the resin sliding member 17 come into contact with the metal slide bearing 16 to the outside of an opening 19 of the metal slide bearing 16. That is, if the protrusions 18 are formed facing the opening 19 of the metal slide bearing 16 when the resin sliding member 17 slides over the metal slide bearing 16, the resin sliding member 17 will be worn down by the edges of this opening 19. To avoid this, as discussed above, the protrusions 18 at the side portions of the resin sliding member 17 come into contact with the metal slide bearing 16 to the outside of the opening 19 of the metal slide bearing 16.

As can be seen in FIG. 2, the through-hole 9 in the main body case 1 is provided inside a recess 20 that is provided to the main body case 1 and used for housing the manipulation component, and both the through-hole 9 and the recess 20 for housing the manipulation component are formed longer in the manipulation direction of the manipulation component 15.

Also, as discussed above, the annular wall 10 is formed protruding outside the main body case 1 and around the through-hole 9, but as shown in FIG. 2, the sensor insertion opening 3 side of this annular wall 10 is semicircular. Accordingly, the metal slide bearing 16 and the resin sliding member 17 are both semicircular on the sensor insertion opening 3 side, as shown in FIGS. 2, 6A, and 6B. When the sensor insertion opening 3 side of the resin sliding member 17 comes into contact with the sensor insertion opening 3 side of the metal slide bearing 16, this restricts the movement position of the manipulation component 15 to the display component 5 side, which is the opposite side from the sensor insertion opening 3.

That is, the shape of the resin sliding member 17 and the shape of the metal slide bearing 16 are both semicircular on the sensor insertion opening 3 side, and the movement position of the manipulation component 15 is restricted by the metal slide bearing 16.

In this embodiment, the through-hole 9, the annular wall 10, the metal slide bearing 16, and the resin sliding member 17 are semicircular on their sensor insertion opening 3 side as mentioned above, but their shape may instead be square or elliptical.

Also, in this embodiment, the annular wall 10 is provided as a base for providing the metal slide bearing 16. This annular wall 10 is provided protruding out of the main body case 1 on the outside of the through-hole 9 of the main body case 1. Therefore, any water, alcohol, or other liquid used for cleaning the main body case 1, for example, will be less likely to infiltrate the interior of the main body case 1 from the through-hole 9.

Sine the annular wall 10 is provided in the form of a ring, the metal slide bearing 16 that covers this annular wall 10 is also annular.

Also, in this embodiment, The resin sliding member 17 and the manipulation component 15 were configured separately, but the manipulation component 15 may instead be formed integrally with the resin sliding member 17.

Also, the resin sliding member 17 is formed from POM, which is a resin with good sliding properties, for example. POM is an acronym for the chemical name polyoxymethylene, but POM is generally called an acetal resin or a polyacetal resin, and refers to a crystalline thermoplastic resin composed mainly of oxymethylene structural units.

The metal slide bearing 16 is formed from stainless steel, for example, but may be formed from any other metal that is resistant to corrosion, and may be plated with a metal on the surface. Naturally, the product of metal plating the surface of the resin annular wall 10 can also be treated as this metal slide bearing 16.

Also, in this embodiment, the height of the annular wall 10 is lower than the recess 20 used to house the manipulation component, and in a state in which the metal slide bearing 16, the resin sliding member 17, and the manipulation component 15 are provided above, the manipulation component 15 sticks out slightly above the recess 20 used to house the manipulation component.

INDUSTRIAL APPLICABILITY

As discussed above, the sensor discharge mechanism of the present invention is expected to find wide application as a biological information measurement device for measuring biological information from blood, such as a blood glucose level.

The invention claimed is:

1. A biological information measurement device that can connect to a sensor, the biological information measurement device comprising:
   a main body case including a sensor insertion opening, a sensor connector, and a sensor discharge mechanism;
   the sensor insertion opening including a rear portion;
   the sensor connector provided to the rear portion of the sensor insertion opening;
   the sensor discharge mechanism configured to discharge the sensor mounted to the sensor connector through the sensor insertion opening, the sensor including a rear part;
   the sensor discharge mechanism including an engagement component, a manipulation body, a manipulation rod, a manipulation component, an annular wall, and a metal slide bearing;
   the engagement component configured to engage with the rear part of the sensor when the sensor is mounted to the sensor connector;
   the manipulation body configured to move the engagement component towards the sensor insertion opening;
   the manipulation rod including a first end and a second end, the first end engaged with the manipulation body, and the second end configured to be pulled out of the main body case through a through-hole of the main body case;
   the manipulation component linked to the second end of the manipulation rod, the manipulation component including a metal slide bearing;
   the annular wall disposed on an outside of the main body case and around the through-hole;
   the metal slide bearing covering the annular wall; and
   a resin sliding member provided on the second end of the manipulation component, the resin sliding member configured to slide respective to the metal slide bearing.

2. The biological information measurement device according to claim 1, wherein:
   the manipulation component and the resin sliding member are separate members, and
   the resin sliding member is integrally attached to the manipulation component.

3. The biological information measurement device according to claim 1, wherein:
   the metal slide bearing includes a face;
   the manipulation component further includes a manipulation direction, the manipulation direction being a direction in which the manipulation component is manipulated; and
   the resin sliding member further includes two side portions, each side portion including a protrusion, the two side portions arranged in a direction perpendicular to the manipulation direction, each protrusion extending towards the metal slide bearing, and in contact with the face of the metal slide bearing.

4. The biological information measurement device according to claim 3, wherein:
   the metal slide bearing further includes an opening, and
   the protrusions of the resin sliding member contact the metal slide bearing outside the opening of the metal slide bearing.

5. The biological information measurement device according to claim 1, wherein:
   the main body case further includes a recess,
   the manipulation component is housed in the recess, and
   the through-hole in the main body case is formed in the recess.

6. The biological information measurement device according to claim 1, wherein:
   the manipulation component further includes a manipulation direction, the manipulation direction being a direction in which the manipulation component is manipulated, and
   the through-hole is longer in the manipulation direction than in a direction perpendicular to the manipulation direction.

7. The biological information measurement device according to claim 6, wherein:
   the through-hole further includes a sensor insertion opening side, and
   the through-hole is semicircular on the sensor insertion opening side.

8. The biological information measurement device according to claim 1, wherein:
   the metal slide bearing includes a face;
   the manipulation component further includes a manipulation direction, the manipulation direction being a direction in which the manipulation component is manipulated; and
   the resin sliding member further includes two side portions, each side portion including a protrusion, the two side portions arranged in a direction perpendicular to the manipulation direction, each protrusion extending towards the metal slide bearing, and in contact with the face of the metal slide bearing.

9. The biological information measurement device according to claim 8, wherein:

the metal slide bearing further includes an opening, and the protrusions of the resin sliding member contact the metal slide bearing outside the opening of the metal slide bearing.

10. The biological information measurement device according to claim 2, wherein:

the main body case further includes a recess, the manipulation component is housed in the recess, and the through-hole in the main body case is formed in the recess.

11. The biological information measurement device according to claim 2, wherein:

the manipulation component further includes a manipulation direction, the manipulation direction being a direction in which the manipulation component is manipulated, and the through-hole is longer in the manipulation direction than in a direction perpendicular to the manipulation direction.

12. The biological information measurement device according to claim 11, wherein:

the through-hole further includes a sensor insertion opening side, and the through-hole is semicircular on the sensor insertion opening side.

* * * * *